July 4, 1950 F. MEILLAND Plant Pat. 961
ROSE PLANT
Filed April 4, 1949
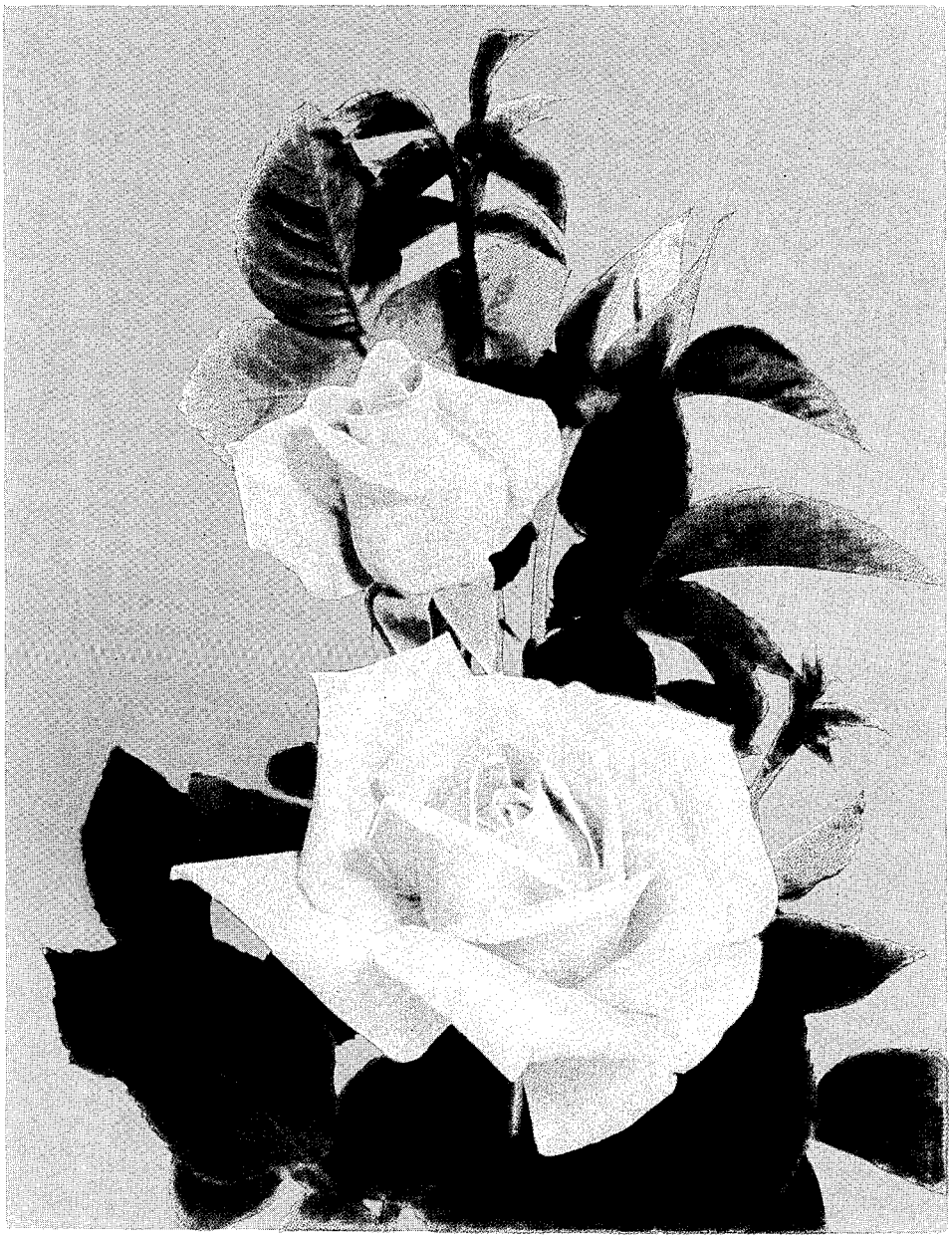
Inventor
By F. Meilland
Robb & Robb
by A. E. Robb
attorneys Patented July 4, 1950

UNITED STATES PATENT OFFICE

961

ROSE PLANT

Francis Meilland, Cap Azura, Cap d'Antibes, France, assignor to The Conard-Pyle Company, West Grove, Pa., a corporation of Pennsylvania Application April 4, 1949, Serial No. 85,400

1 Claim. (Cl. 47—61)

The present invention relates to a new and distinct variety of rose plant with a novel combination of characteristics not heretofore found in roses known to the trade at the present time.

This new variety is distinguished from others of the same class by its habit of growing into a very strong, upright plant with healthy foliage, a very free bloomer, with pointed buds, and large open flowers that are extremely showy. These flowers are silvery pink in color and consistently superior in their unvarying perfection of form at all seasons.

Asexual reproduction of this new variety by budding at Tassin-les-Lyon, Rhone, France, and at West Grove, Pennsylvania, shows the foregoing characteristics come true to form and are established.

In the accompanying drawing are illustrated specimens of the blooms from the bud stage to the full blown flowers showing their perfection of form, and the foliage and the strong, healthy stems on which the blooms are borne.

The following is a detailed description of the new variety, all reference to color being in accordance with Ridgway's Color Standards and Nomenclature:

Type: Hardy; bush; outdoor; seedling; for cut flowers and garden decoration.
Class: Hybrid tea.
Breeding: Seedling. "Radiance" × "Dame Edith Helen" (both unpatented).
Propagation: Holds its distinguishing characteristics through succeeding propagations by budding.

*Flower*

Locality where grown: West Grove, Pennsylvania.
Flowers borne: Singly to stem; on strong, medium length stems.
Quantity of bloom: Free.
Continuity: Continuous.
Fragrance: Moderate; tea.
Bud:
*Peduncle.*—Medium length; medium heavy; erect; medium number of yellow brown prickles. Color—Lettuce Green, Plate V.
*Before calyx breaks.* — Size — medium. Form—pointed; ovoid; with foliaceous appendages on the surface of the bud; with cut foliaceous parts extending beyond the tip of the bud equal to one-fourth or more of its length.
*As calyx breaks.* — Color — Eosine Pink, Plate I.
*As first petal opens.*—Size—medium large.

Form—pointed. Color—outside: Pale Green Yellow at base shading to Jasper Pink, Plate XIII, and to Old Rose, Plate XIII, near outer edges; inside: Picric Yellow, Plate IV, at base tip; light Rose Red, Plate XII, over most of petal.
*Opening.*—Opens up well.
Bloom: Size, when fully open—large; five inches to six inches.
*Petalage.*—Double; from 25 to 30 petals arranged regularly.
*Form.*—Very high center at first; becoming high centered; petals remaining at first very loosely rolled outward; becoming later, at maturity, loosely rolled outward.
Petals: Leathery; with inside and outside satiny.
*Shape.*—Outside — obovate. Intermediate—obovate. Inside—obovate.

This description of a newly opened flower was made from a rose grown outdoors in the month of August, at West Grove, Pennsylvania:

*Color.—Outside petal*—outside surface: Alizarine Pink, Plate XIII (Pale Green Yellow, Plate V, at base); inside surface: Rose Color, Plate XII (Picric Yellow, Plate IV, at base). *Intermediate petal*—outside surface: Dark Thulite Pink, Plate XXVI (Sulphur Yellow, Plate V, at base); inside surface: Rose Red Color, Plate XII (Light Green Yellow, Plate V, at base). *Inner petal*—outside surface: Light Rose Color, Plate XII (Pale Green Yellow, Plate V, at base); inside surface: Light Rose Red, Plate XII (Light Green Yellow, Plate V, at base).

This description was made from a rose that was open for three days outdoors in the month of August, at West Grove, Pennsylvania:

*Color.*—Outside petal—outside surface: Pale Dull Green Yellow, Plate XVII, at base shading to white and Rose Pink, Plate XII, over most of petal; inside surface: Deep Rose Pink, Plate XII (Pale Viridine Yellow, Plate V, at base). *Inside petal*—outside surface: Rose Pink, Plate XII (white at base); inside surface: Deep Rose Pink, Plate XII (Pale Greenish Yellow, Plate V, and white at base).
*General color effect.*—Newly opened flower—Rose Color, Plate XII. Three days open—Deep Rose Pink, Plate XII, to Rose Color, Plate XII.
*Behavior.*—Drop off cleanly.
*Flower longevity.*—Cut roses grown outdoors kept at living-room temperatures, five to six days in August.

*Reproductive organs*

Stamens: Many; arranged regularly about pistils.
Filaments: Medium long; most with anthers. Color—Pinard Yellow, Plate IV.
Anthers: Large; all open at various times; occasionally an anther fused with a petaloid. Color—Light Cadmium Yellow, Plate IV, with Maize Yellow, Plate IV, center stripe.
Pollen: Abundant. Color — Cadmium Yellow, Plate III.
Pistils: Medium number.
Styles: Uneven; medium thin; bunched.
Stigma: Color—Sulphur Yellow, Plate IV.
Ovaries: Some protruding from calyx.
Hips: Short; smooth; walls medium thick. Color—Oil Green, Plate V.
Sepals: Permanent; moderately long; spear-shaped.
Seeds: Few; small.

*Plant*

Foliage:
*Leaves.*—Compound of three or five leaflets; abundant; medium large; leathery.
*Leaflets.*—Shape, oval with apex acute; base round; margin simply serrate.
*Color.*—*Mature*—upper surface: Dark Cress Green, Plate XXXI; under surface: Pois Green, Plate XLI. *Young*—upper surface: Parrot Green, Plate VI, veiled with Claret Brown, Plate I; under surface: Mineral Red, Plate XXVII.
*Rachis.*—Medium heavy. Upper side:

grooved; prickly; under side: sparsely thorny.
*Stipules.*—Medium length; medium width; medium length points turning out at an angle of less than 90°.
Disease: Resistant to mildew and blackspot.
Growth:
*Habit.*—Upright; branched moderately.
*Growth.*—Vigorous.
*Canes.*—Medium heavy.
*Main stems.*—Dull green occasionally tinged with red. *Thorns*—several; medium length; hooked downward; with medium length narrow base. Incipient thorns among large ones. *Prickles*—few; brown. *Hairs*—none.
*Branches.*—Gray green sometimes tinged with red. *Thorns* — several; medium length; hooked downward; with medium length narrow base. Incipient thorns among large ones. *Prickles*—few; green-reddish. *Hairs*—none.
*New shoots.*—Color, Lettuce Green, Plate V. *Thorns*—several; medium length; hooked downward; with short narrow base. *Prickles and hairs*—none.

I claim:

A new and distinct variety of rose plant characterized as to novelty by its strength, uprightness of growth, its healthy foliage, its free blooming habit, its production of pointed buds and large, open and showy flowers of silvery pink color, and consistently perfect form at all seasons, substantially as shown and described.

FRANCIS MEILLAND.

No references cited.